US00PP28596P3

(12) United States Plant Patent
Bradford et al.

(10) Patent No.: US PP28,596 P3
(45) Date of Patent: Nov. 7, 2017

(54) PLUM TREE NAMED 'PLUMSWEET XIX'

(50) Latin Name: *Prunus salicina*
Varietal Denomination: PLUMSWEET XIX

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 23 days.

(21) Appl. No.: 14/757,254

(22) Filed: Dec. 11, 2015

(65) Prior Publication Data

US 2017/0172026 P1 Jun. 15, 2017

(51) Int. Cl.
*A01H 5/08* (2006.01)

(52) U.S. Cl.
USPC ..... Plt./184

(58) Field of Classification Search
USPC ..... Plt./184
See application file for complete search history.

(56) References Cited

U.S. PATENT DOCUMENTS

PP23,686 P2 6/2013 Bradford

*Primary Examiner* — Keith Robinson

(57) ABSTRACT

The present invention relates to a plum tree, *Prunus salicina*, and more particularly to a new and distinct variety broadly characterized by a medium size, moderately vigorous, hardy, and productive tree. Being self-unfruitful, the present variety requires cross pollination from an apricot, interspecific, or plum that blooms during the mid season, such as 'September Yummy' plum tree (U.S. Plant Pat. No. 14,220). The present variety's abundance of blossoms and moderate pollen production entices strong bee activity to facilitate pollination. The fruit matures under the ecological conditions described during mid to late July, with first picking on Jul. 13, 2015, and will hang on the tree for at least three weeks. The fruit is uniformly medium in size, red over a green background with dark red dappling in skin color, clingstone in type, globose to oblate with some asymmetry in shape, full red in flesh color, very firm and crisp in texture, very sweet, and excellent in flavor.

1 Drawing Sheet

Botanical classification: *Prunus salicina.*
Varietal denomination: 'PLUMSWEET XIX'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree, which has been denominated varietally as 'PLUMSWEET XIX'.

During a typical blooming season we isolate as seed parents both individual and groups of different plum and interspecific hybrid trees by covering them with screen houses. A hive of bees is placed inside each such house, and bouquets to provide pollen from different plum, apricot, and interspecific hybrid trees are placed in buckets near the trees approximately every two days for the duration of the bloom. During 2008 one tree of 'OC579' (unpatented) plum was crossed by us in this manner. To pollinate this isolated tree, we selected bouquets from several sources of plum trees without keeping specific written details. Upon reaching maturity the fruit from this plum tree was harvested, and the seeds were removed, cracked, stratified and germinated as a group with the label "H1". They were grown as seedlings on their own root in our greenhouse and upon reaching dormancy transplanted to a cultivated area of our experimental orchard located near Le Grand, Calif. in Merced County (San Joaquin Valley). During the summer of 2012 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'OC579' plum (unpatented), by being self-unfruitful and by producing fruit that is firm, juicy, sweet, and medium in size, but is quite distinguished therefrom by producing fruit that is dark red and green in skin color instead of pink and yellow, that is much darker red in flesh color, and that matures about forty days earlier.

The present variety is most similar to 'Plumsweet XIV' (U.S. Plant Pat. No. 23,686) interspecific tree by being self-unfruitful, by blooming in the mid season, and by producing fruit that is sweet and excellent in flavor, primarily a red and green two-tone in skin color, and clingstone in type, but is quite distinguished therefrom by producing fruit that is larger in size, that is moderately asymmetrical in shape, that has dark red dappling on the skin, and that matures about seven days later.

SUMMARY OF VARIETY

The present plum variety is characterized by a medium size, moderately vigorous, hardy, and productive tree. Being self-unfruitful, the present variety requires cross pollination from an apricot, interspecific, or plum that blooms during the mid season, such as 'September Yummy' plum tree (U.S. Plant Pat. No. 14,220). The present variety's abundance of blossoms and moderate pollen production entices strong bee activity to facilitate pollination. The fruit matures under the ecological conditions described during mid to late July, with first picking on Jul. 13, 2015, and will hang on the tree for at least three weeks. The fruit is uniformly medium in size, red over a green background with dark red dappling in skin color, clingstone in type, globose to oblate with some asymmetry in shape, full red in flesh color, very firm and crisp in texture, very sweet, and excellent in flavor.

DRAWING

The accompanying photograph consists of four whole fruits positioned to display the characteristics of the skin color and form, one divided fruit to reveal the flesh and stone, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif. The fruit description was developed at the state of firm ripe on Jul. 16, 2015, on the original tree during its seventh growing season. The flower and bud descriptions were developed during the previous blooming season. All major color code designations are by reference to the Inter-Society Color Council, National Bureau of Standards. Common color names are also used occasionally.

It is to be noted that the 2015 fruit season in California was very warm during the spring and the ripening times of almost all varieties were about twenty days earlier than other years.

PARENTAGE

Seed parent: 'OC579' plum (unpatented).
Pollen parent: Unknown.

TREE

Size: Medium, reaching and maintaining a height of 9' [2.74 m.] and a spread of 4' [1.22 m.] after seven growing seasons utilizing typical dormant pruning.

Vigor: Moderately vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Central leader type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid seasonal blooming plum or interspecific, such as 'September Yummy' plum tree (U.S. Plant Pat. No. 14,220).

Bearing: Regular bearer, weather dependent, no crop failures observed as of yet.

Trunk:

*Size*.—Stocky, reaching a maximum diameter of 4½" [114 mm.] after the seventh growing season.

*Texture*.—Shaggy.

*Bark color*.—A Grayish brown [61. gy.Br] and Dark grayish brown [62. d.gy.Br] variegation with Dark brown [59. d.Br] crevices present.

*Lenticels*.—Approximate Number Per Square Inch: 6. Color: Brownish gray [64. brGy]. Average Size: 5/16" [7.9 mm.] in length. The width is typically one fourth as much as the length. Shape: Eye-shaped.

Branches:

*Size*.—Medium to slender, diameter of first side hanger is ⅞" [22 mm.] measured 6" from the central leader.

*Texture*.—Smooth to medium roughness on first and second year wood, increasing roughness with age.

*Color*.—1st Year Wood Topside: Grayish red [19. gy.R]. 1st Year Wood Underside: Brilliant yellow green [116. brill.YG]. 2$^{nd}$ Year Wood: A Dark grayish brown [62. d.gy.Br] and Strong brown [55. s.Br] variegation.

*Lenticels*.—Number Per Square Inch: About 25 on second year wood. Color: Light yellowish brown [76. l.yBr]. Average Size: Small, 1/32" [0.8 mm.] in length. The width is typically one fourth as much as the length. Shape: Eye-shaped.

Leaves:

*Size*.—Medium. Average Length: 3¾" [95.3 mm.]. Average Width: 1 ⅜" [34.9 mm.].

*Arrangement*.—Alternate.

*Thickness*.—Medium.

*Form*.—Elliptical.

*Apex*.—Acuminate.

*Base*.—Acute with an average base angle of 60 degrees.

*Surface*.—Smooth on both sides.

*Color*.—Dorsal Surface: Moderate olive green [125. m.OlG]. Ventral Surface: Moderate yellow green [120. m.YG].

*Margin*.—Finely serrate.

*Venation*.—Pinnately net veined.

*Petiole*.—Average Length: ½" [12.7 mm.]. Average Thickness: 1/16" [1.6 mm.]. Color: Topside is Moderate reddish brown [43. m.rBr] and the underside is Grayish greenish yellow [105. gy.gY].

*Stipules*.—Number: Typically 2 per leaf, up to 6 per growing tip. Average Length: ¼" [6.4 mm.]. Color: Brilliant yellow green [116. brill.YG] becoming Dark yellowish brown [78. d.yBr] with age.

*Glands*.—Number: Mostly 2 per leaf. Position: Mostly alternately positioned near the intersection of the petiole and the leaf blade. Form: Globose. Size: Small, 1/64" [0.4 mm.] in diameter. Color: Brilliant yellow green [116. brill.YG] becoming Dark yellowish brown [78. d.yBr] in the center with age. Leaf buds: Pointed.

Flower buds:

*Hardiness*.—Hardy, with respect to central California blooming season.

*Diameter*.—Typically 3/16" [4.8 mm.] 1 week before bloom.
*Length*.—Typically 3/8" [9.5 mm.] 1 week before bloom.
*Form*.—Not appressed.
*Surface*.—Slightly pubescent.
*Tip color*.—White [263. White].

Flowers: Perfect, complete, perigynous, usually a single pistil, typically thirty or more stamens, five sepals and petal locations alternately positioned.
*Average flower diameter*.—1 1/16" [27.0 mm.].
*Average flower depth*.—3/8" [9.5 mm.] when fully open.
*Average pedicel length*.—3/16" [4.8 mm.].
*Number of petals*.—Five, no double blossoms observed.
*Petal shape*.—Oval to circular.
*Petal margin*.—Entire, somewhat wavy.
*Average petal diameter*.—1/2" [12.7 mm.].
*Average petal length*.—9/16" [14.3 mm.].
*Petal apex*.—Rounded.
*Petal base*.—Obtuse.
*Petal color*.—White [263. White] on both sides.
*Anther color*.—Light yellow [86. l.Y].
*Pollen production*.—Moderate, bee enticing.
*Pollen color*.—Strong yellow [84. s.Y].
*Stigma color*.—Light greenish yellow [101. l.gY].
*Stigma position*.—Located slightly below the surrounding anthers.
*Sepal color*.—Brilliant yellow green [116. brill.YG] on both sides.
*Sepal length*.—7/32" [5.6 mm.].
*Sepal width*.—3/16" [4.8 mm.].
*Sepal apex*.—Rounded to elliptical to match the width and length.
*Sepal margin*.—Fairly smooth to the naked eye, slightly serrate when magnified.
*Average pistil length*.—9/16" [14.3 mm.], some blanks observed.
*Average stamen length*.—9/16" [14.3 mm.].
*Ovary*.—Smooth.
*Fragrance*.—Moderate.
*Blooming period*.—Medium compared to other varieties, two days before 'Santa Rosa' plum (unpatented).
*Onset of bloom*.—One percent on Feb. 16, 2015.
*Date of full bloom*.—Feb. 27, 2015.
*Duration of bloom*.—One to two weeks, dependent on ambient temperature.
*Bloom density*.—Heavy.
*Number per cluster*.—2 to 8, average 4.

FRUIT

Maturity when described: Firm ripe, Jul. 16, 2015.
Date of first picking: Jul. 13, 2015.
Date of last picking: Aug. 4, 2015.
Size: Uniform, Medium.
*Average diameter axially*.—2 3/8" [60.3 mm.].
*Average diameter across cheek plane*.—2 3/4" [69.9 mm.].
*Average diameter across suture plane*.—2 5/8" [66.7 mm.].
*Typical weight*.—5.9 ounces [167 grams].

Form: Uniform, globose to oblate, compressed axially toward the suture, moderately asymmetrical.
*Longitudinal section form*.—Round to oblate.
*Transverse section through diameter*.—Round.

Suture: A distinct Moderate yellow green [120. m.YG] line located in a shallow groove extending from the base to the apex.
Ventral surface: Rounded, lipped slightly throughout.
Lips: Somewhat unequal.
Cavity: Flaring and circular, suture showing on one side.
*Depth*.—1/2" [12.7 mm.].
*Breadth*.—1 1/8" [28.6 mm.].
Base: Truncate, cordate if viewed parallel to the suture.
Apex: Rounded, protruding on one side.
Pistil point: A Grayish reddish brown [46. gy.rBr] dot.
Stem: Medium.
*Average length*.—3/8" [9.5 mm.].
*Average width*.—1/16" [1.6 mm.].

Skin:
*Thickness*.—Medium.
*Surface*.—Smooth.
*Tenacity*.—Tenacious to the flesh.
*Astringency*.—Moderate.
*Tendency to crack*.—Occasional shoulder tear observed.
*Color*.—Moderate red [15. m.R] over a Moderate yellow green [120. m.YG] background with heavy Very dark red [17. v.d.R] dappling throughout and heavy Light orange yellow [70. l.OY] freckling stronger toward the apex.
*Lenticels*.—Number Per Square Inch: About 160 toward the apex. Average diameter: 1/64" [0.4 mm].
*Bloom*.—Moderate to heavy.

Flesh:
*Color*.—Very deep red [14. v.deep R] toward the skin and Dark pink [6. d.Pk] toward the stone with Deep red [13. deep R] veins present throughout.
*Surface of pit cavity*.—Covered with Dark red [16. d.R] broken fibers when twisted away from stone.
*Amygdalin*.—Moderate.
*Juice*.—Abundant, rich.
*Texture*.—Firm, crisp, meaty, can hung firm on the tree for up to three weeks.
*Fibers*.—Abundant.
*Ripens*.—Slightly earliest along shoulder.
*Flavor*.—A tasty blend of acid and sugar, very sweet, typically 18 to 22 brix.
*Aroma*.—Slight.
*Eating quality*.—Excellent.

STONE

Type: Clingstone.
Form: Obovate.
Hilum: Narrow, oval.
Base: Truncate.
Apex: Obtuse with a sharp 1/8" [3.2 mm.] tip.
Sides: Equal.
Surface: Rough throughout with one groove on each side of the dorsal fin.
External color of stone: Dark orange yellow [72. d.OY].
Pit wall color when cracked: Light grayish yellowish brown [79. l.gy.yBr].
Cavity surface color: Light yellowish brown [76. l.yBr].
Average pit wall thickness: 1/8" [3.2 mm.].
Average length: 7/8" [22.2 mm.].
Average width: 3/4" [19.1 mm.].
Average breadth: 3/8" [9.5 mm.].

Tendency to split: None observed.
Kernel:

*Form*.—Oval.
*Skin color*.—Pale yellow [89. p.Y].
*Pellicle color*.—Strong yellowish brown [74. s.yBr].
*Vein color*.—Grayish yellow [90. gy.Y].
*Taste*.—Bitter.
*Viable*.—Yes.
*Average length*.—⅜" [9.5 mm.].
*Average width*.—¼" [6.4 mm.].
*Amygdalin*.—Moderate.

USE

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: Not tested.
Resistance to diseases: Not tested.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, substantially as illustrated and described, that is most similar to 'Plumsweet XIV' (U.S. Plant Pat. No. 23,686) interspecific tree by being self-unfruitful, by blooming in the mid season, and by producing fruit that is sweet and excellent in flavor, primarily a red and green two-tone in skin color, and clingstone in type, but is quite distinguished therefrom by producing fruit that is larger in size, that is moderately asymmetrical in shape, that has dark red dappling on the skin, and that matures about seven days later.

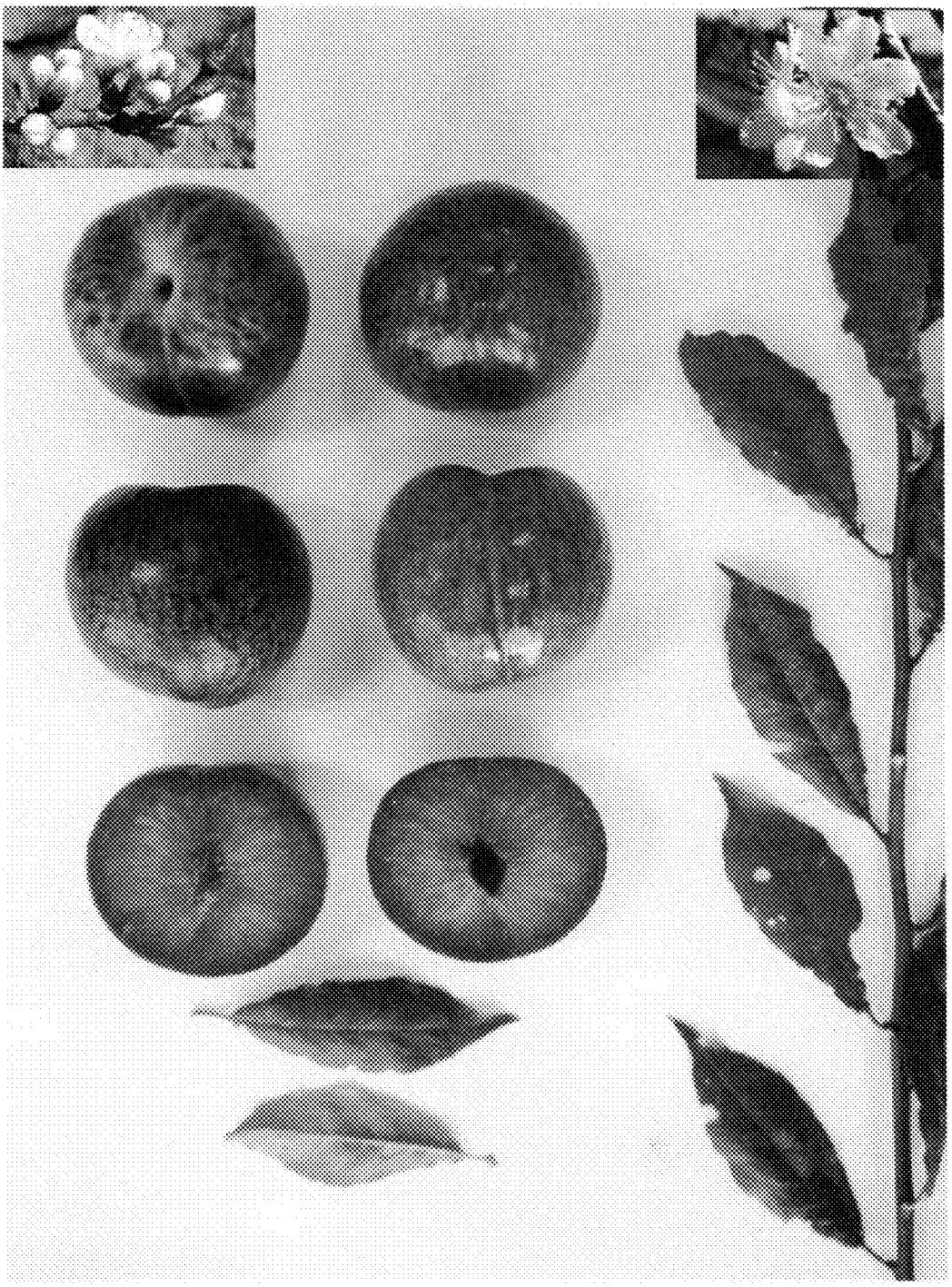

* * * * *